(12) United States Patent
Gee et al.

(10) Patent No.: US 8,877,892 B2
(45) Date of Patent: Nov. 4, 2014

(54) CONJUGATION REACTIONS

(75) Inventors: Nicholas Gee, Essex (GB); Annamaria Draghi, Asiago (IT)

(73) Assignee: Innova Biosciences Limited, Cambridge (GB)

( * ) Notice: Subject to any disclaimer, the term of this patent is extended or adjusted under 35 U.S.C. 154(b) by 78 days.

(21) Appl. No.: 13/048,477

(22) Filed: Mar. 15, 2011

(65) Prior Publication Data

US 2012/0237998 A1    Sep. 20, 2012

(51) Int. Cl.
| | | |
|---|---|---|
| *A61K 38/00* | (2006.01) | |
| *C08L 5/02* | (2006.01) | |
| *C12N 9/00* | (2006.01) | |
| *C07K 14/765* | (2006.01) | |
| *C08B 37/02* | (2006.01) | |
| *C09D 105/02* | (2006.01) | |
| *C09K 11/02* | (2006.01) | |
| *B65D 85/84* | (2006.01) | |
| *C08L 21/02* | (2006.01) | |

(52) U.S. Cl.
CPC . *B65D 85/84* (2013.01); *C08L 5/02* (2013.01); *C12N 9/00* (2013.01); *C07K 14/765* (2013.01); *C08B 37/0021* (2013.01); *C09D 105/02* (2013.01); *C09K 11/02* (2013.01); *C08L 21/02* (2013.01)
USPC ............................ 530/338; 530/340; 530/341

(58) Field of Classification Search
CPC ...... C09K 11/02; B65D 85/84; C07K 14/765; C08L 5/02; C08L 21/02; C08B 37/0021; A61K 47/48038; C07H 13/02
USPC ............... 435/188; 530/345, 391.3, 338, 340, 530/341; 536/112
See application file for complete search history.

(56) References Cited

U.S. PATENT DOCUMENTS 5,739,350 A * 4/1998 Kelly et al. .................... 548/421

FOREIGN PATENT DOCUMENTS

| WO | WO-00/43784 A1 | 7/2000 |
| WO | WO-2005/044923 A1 | 5/2005 |

OTHER PUBLICATIONS

Bodanszky et al. Journal of Am. Chem. Soc. 81, 5688-5691 (1959).*
Kisfaludy et al. Journal of Org. Chem. 35, 3563-3565 (1970).*
Search report from GB1003697.8, Search date: Sep. 2010.
Uptima,"EDAC (carbodiimide)" [online]. Published Oct. 16, 2007. Available from http://web.archive.org/web/20071016180225/http://vwvw.interchim.com/interchimlbio/produitsuptima/tech_sheet/FT-UP52005(EDC).pdf, [Accessed Sep. 9, 2010]. See especially "Protocole 2". Author is not available.
"A Modular Approach . . . ", Bioconjugate Chem. 2004, 15, 583-593, Skrzypczynski et al. See especially synthesis of compounds 3, 4a and 11 p. 584.
Barrett and Elmore, "Amino Acids and Peptides", published 1998, Cambridge University Press. See pp. 153-154.
"Chemical Peptide Synthesis" [online], published Jan. 28, 2009. Available from http://mason.gmu.edul—bbishopl/chem468/Chem468-SPPS.pdf [Accessed Sep. 10, 2010]. Author is not available.
Innova Biosciences, "A Revolution in Conjugation Technology" [online]. Published May 13, 2007. Available from http://web.archive.org/web/20070513032615/http://web.archive.org/web/20070513032615/http://www.innovabiosciences.com/products/lightninglink.php [Accessed Sep. 9, 2010]. Author is not available.
"Synthesis of Coumarin . . . ", J. Heterocyclic Chem. 32, 1995, 573-577, See especially Scheme 2 and Experimental section relating to compounds 7a-i (pp. 575 and 577). Bonsignore et al.
"A new method for conjugation . . . ", Bioorganicheskaya Khimiya, 1989, 15(11), 1480-3 and STN CAPLUS abstract accession No. 1990:34145. Pikuleva et al.
BioAssay Works; Latex-in-a-Box; downloaded from http://archive.org/web/; Apr. 10, 2009, Author is not available.
Covalent Coupling Procedure on fluidMAG-PAS by Carbodiimide Method; downloaded from http://archive.org/web/; Aug. 21, 2009, Author is not available.
Hermanson; Bioconjugate Techniques; 1996; p. 177; Academic Press; San Diego, California.

* cited by examiner

*Primary Examiner* — Chih-Min Kam
(74) *Attorney, Agent, or Firm* — Brian R. Dorn; Barnes & Thornburg LLP

(57) ABSTRACT

We describe methods that allow either carbodiimides or other carboxyl-reactive substances to be mixed with solutions of carboxylic acids or phosphates or amines or combinations thereof, so as to form a homogeneous mixture which is then dried, preferably in a freeze drying process. The mixture is then contacted with an entity, which preferably involves the dissolution of the mixture with a buffered solution of the entity, so as to initiate a conjugation reaction between the entity and a component in the mixture.

20 Claims, 7 Drawing Sheets

US 8,877,892 B2

CONJUGATION REACTIONS

FIELD OF THE INVENTION

This invention relates to conjugation reactions between a reactant containing a carboxyl group or phosphate group (particularly a phosphate (V) group) and a reactant containing an amine group, and concerns reagents for use in such a reaction.

BACKGROUND TO THE INVENTION

It is known how to conjugate a reactant containing a carboxyl group with a reactant containing an amine group using a carboxyl-activating reagent such as a carbodiimide ($R_1N=C=NR_2$), which acts as a zero-length cross-linker.

The reaction of carbodiimides with carboxyl groups is one of the most important and is used for coupling of molecules or biomolecules to a variety of surfaces, including supports for affinity chromatography; for derivatising latex microparticles that are used in lateral flow tests or agglutination assays; and for derivatising chip surfaces in order to study molecular interactions using surface plasmon resonance. Carbodiimides have also been used to quantify carboxyls in proteins, and for covalently linking antigens/analytes to carrier proteins to enhance immunogenicity.

The reaction of carbodiimides with carboxyl groups generates a highly unstable o-acylisourea which may further react with amines to form amides. In the absence of amino groups the o-acylisourea reacts either with another molecule of acid to form an anhydride or undergoes an intramolecular O-to-N acyl rearrangement to form a stable N-acylurea. In aqueous solutions (but not in organic solvents) the o-acylisourea is rapidly hydrolysed by water (concentration ~55M), regenerating the original carboxyl group and converting the carbodiimide into an unreactive substituted urea. Because of competition with water molecules it may be difficult for amines to react to form amides unless the amine precursor it present at a high concentration. Finally, in the absence of carboxyl groups, carbodimides may react with amines to form guanidines.

One of the major applications of carbodiimides is in the field of bioconjugation, whereby carboxyl functions on one entity (e.g. a protein, a microparticle or a chip surface) are activated and then reacted with amine groups on another entity, often a protein or peptide or analyte to form an amide-linked conjugate. Typically, in such reactions, the carboxylic entity is contacted with the aminated molecule in a buffered solution of pH 4 to pH 6 and a water soluble carbodiimide is added to initiate the conjugation reaction.

Reactions that are performed in organic solvents (e.g. synthesis of peptides) usually employ a hydrophobic carbodiimide such as dicyclohexylcarbodiimide (DCC) or N,N'-diisopropylcarbodiimide (DIC). However, reactions involving biomolecules usually require aqueous conditions, or substantially aqueous solutions, and in these situations a water soluble carbodiimide such as 1-Ethyl-3-[3-dimethylaminopropyl]carbodiimide (EDC; also EDAC) or N-Cyclohexyl-N'-(β-[N-methylmorpholino]ethyl)carbodiimide (CMC) is preferred.

Where it is not possible to achieve a sufficiently high concentration of the amine (for example, because of limited solubility or high cost) it may be possible to increase the efficiency of the conjugation reaction by adding N-hydroxysuccinimide (NHS) to convert the highly unstable o-acylisourea intermediate into a more stable succinimidyl (or 'NHS') ester, which also reacts readily with amines (Staros et. al., Anal. Biochem., 156, 220-222, 1986). NHS may greatly accelerate reactions and precipitate uncontrolled crosslinking of some biomolecules, thus the need for NHS must be determined on a case-by-case basis.

The reaction of EDC with carboxyl groups is most efficient at pH 3.5-4.5 (Nakajima and Ikada, Bonconjugate Chem. 6, p 123-130, 1995). The pH optimum for EDC-mediated amide bond formation is often a little higher, usually between pH 4 and pH 6. This optimum reflects a balance of a number of factors, including the rate of formation and hydrolysis of the o-acylisourea and the pKa of the amine nucleophile, which may be substantially above the pH at which the o-acylisourea intermediate is preferentially formed.

In view of the potential reaction of amines with EDC in the absence of carboxyl groups, the amine is not normally contacted with EDC before addition of the carboxylated species, assuming the objective is to form an amide bond, though it is common practice to add freshly prepared EDC to solutions comprising both amine- and carboxyl-containing substances. Such reaction mixtures ideally lack other components with functional groups that could react with the carbodiimide or o-acylisourea intermediate.

An analogous approach to increase reaction efficiency in carbodiimide-mediated condensation reactions between phosphate groups and amines uses methylimidazole as a stabiliser.

Carbodiimides are generally considered to be unstable in aqueous solution.

For example, EDC is widely characterised as a highly labile molecule and there are numerous cautionary notes in the prior art about the need to use freshly prepared solutions of EDC in bioconjugation reactions.

For example, Bioconjugate Techniques (G T Hermanson 1996; ISBN 0-12-342335-x; p 170) states " . . . the stock solution should be dissolved rapidly and used immediately to prevent extensive loss of activity".

A more recent edition of Bioconjugate Techniques (2008) states that: 'EDC is unstable in aqueous environments and should be used immediately after the solution is made (G T Hermanson 2008; ISBN 978-0-12-370501-3, p 688).

In a procedure for conjugation of carboxyl SiMAG magnetic particles the manufacturer Chemicell GmbH advises the following in protocol A1: "Add only freshly prepared EDC to the particles . . . (text that is underlined is shown in bold in the original protocol).

The protocol for Carboxylink gel (Pierce, product code 20266) states "Note: EDC is moisture sensitive and hydrolyzes quickly when dissolved in aqueous buffers . . . . Dissolve the required amount of reagent quickly and immediately before use, and discard any unused solution."

Sigma-Aldrich product information (EDC, product code E7750) states: "The product is water soluble, but is not stable. It is suggested to prepare a fresh solution immediately before use."

Nanopartz GmbH in describing the correct use of their carboxyl polymer spherical gold nanoparticles conjugation kit states: "Use only the EDC amount necessary—once dissolved in water its lifetime is less than one hour."

Another supplier of microparticles (Seradyn) states in 'Recommended Adsorption and covalent coupling procedures' (1999): "Note that EDAC is very sensitive to moisture and undergoes rapid hydrolysis in aqueous solutions."

EDC is obtained from commercial suppliers typically as the hydrochloride salt and is routinely stored in powdered form in glass bottles usually at −20° C. It is normal practice to store with desiccant and to equilibrate stock bottles to room temperature before opening to avoid moisture condensation inside the bottle.

There have been several studies on the stability of EDC in aqueous environments (Gilles et al., Anal. Biochem. 184, p 244-248, [1990]; Nakajima and Ikada, Bioconjugate chemistry, 6, 123-130 [1995]; Williams and Ibrahim; J. Am. Chem. Soc. 103, 7090-7095 [1981]; Lei et al., Anal Biochem. 310, 122-124 [2002]). While the different experimental designs prevent any direct comparison of data, the main findings may be summarised thus:

Decomposition of EDC increases as the pH is reduced from pH 7 to around the values (i.e. around pH 4) at which efficient formation of the o-acylisourea intermediate occurs (Lei et al., Anal Biochem. 310, 122-124 [2002]). Acid catalysed hydrolysis of EDC to the corresponding urea is the major pathway for loss in acidic media. Indeed, reactions involving EDC are sometimes quenched with HCl. A lower rate of decomposition of EDC has been observed in alkaline buffers (Nakajima and Ikada; Bonconjugate Chem. 6, p 123-130, 1995) though Williams and Ibrahim (J. Am. Chem. Soc. 103, 7090-7095, 1981) recorded high rates of hydrolysis in the presence of sodium hydroxide.

In Methods in Molecular Biology volume 394, Salmonella Methods and Protocols (S A Dunbar & J W Jacobsen; p 15) the following advice is given: "EDC is labile in the presence of water. The active species is hydrolyzed in aqueous solutions at a rate constant of just a few seconds, so care should be taken to minimise exposure to air and moisture".

Hydrolytic decomposition of EDC in aqueous solution is known to be greatly accelerated by the presence of carboxyl groups, which catalyse cycling reactions involving repeated formation and hydrolysis of the highly unstable o-acylisourea intermediate. A 1000-fold increase in the rate of EDC loss in the presence of a tricarboxylic acid (citric acid) was observed at pH 4 (Wrobel et. al., Anal. Biochem. 305, 135-138 [2002]). These authors also showed significant acceleration at pH 4 by monocarboxylic acids (acetate) and phosphate. Catalytic effects of various buffers including Tris, MOPS, and HEPES, were also noted, though the mechanisms of catalysis in these cases were unclear.

Accelerated decomposition is also observed with inorganic phosphate, which is presumed to occur via an unstable o-phosphoisourea derivative (Gilles et al., Anal. Biochem. 184, p 244-248, [1990]), and with adenosine trisphosphate.

Ethylene diamine (which is widely employed in EDC-mediated reactions to introduce amines into carboxylic supports or polymers) and a monoamine, glycine methyl ester, which is used to block/quantify carboxyls, may also accelerate the decomposition of EDC (Gilles et al., Anal. Biochem. 184, p 244-248, [1990].

Hydrolytic decomposition of carbodiimides is not unique to EDC; for example, 1-ethyl-3-(4-azonia-4,4-dimethylpentyl)carbodiimide (EAC) was degraded an order of magnitude more rapidly than EDC in the presence of various additives (Gilles et al., Anal. Biochem. 184, 244-248, [1990]).

The various statements in the prior art with regard to lack of stability of EDC, extreme sensitivity of the o-acylisourea intermediate to hydrolysis and greatly accelerated decomposition in the presence of substances commonly used in bioconjugation reactions (e.g. carboxyl groups) are acknowledged, either implicitly or explicitly, in contemporary EDC conjugation protocols.

Indeed the reported instability of EDC and accelerated decomposition by polycarboxylic acids has undoubtedly shaped some very elaborate procedures for creating dry mixtures containing EDC, for example, methods using temporal spacing of reactants through phase change (U.S. Pat. No. 6,809,186). In this approach, the reactants are combined sequentially by flash freezing solutions and then freeze drying the resulting layered structure to obtain a dry product. This approach is extremely tedious if one wishes to optimize multiple reaction parameters and awkward to scale up for any commercial application. The authors of U.S. Pat. No. 6,809, 186 also refer to 'the short lifetimes of the EDAC at near neutral pH . . . ' (column 8 line 47).

The content of all documents and publications cited in the present specification is specifically incorporated herein by reference.

The present inventors have surprisingly found that carboxyl-activating substances, such as carbodiimides, are not in practice as unstable as is stated repeatedly in the literature, and have used this discovery to develop methods that allow carboxyl-activating substances, such as EDC, to be readily combined with carboxyl- or amine-containing substances (e.g. proteins, small molecules, microparticles) to form homogeneous solutions or suspensions that can be freeze dried without significant decomposition of the various components and used successfully in bioconjugation reactions.

SUMMARY OF THE INVENTION

In one aspect, the invention provides a method of producing a reagent for use in a conjugation reaction between a first reactant containing a carboxyl group or a phosphate group and a second reactant containing an amine group, comprising
a) forming a solution or suspension of
   i) a carboxyl-activating or phosphate-activating non-enzymatic substance capable of acting on a carboxyl group- or phosphate group-containing moiety to facilitate the formation of an amide bond between a carboxyl group and an amine group or a phosphoramidate bond between a phosphate group and an amine group, and
   ii) a first reactant or a second reactant; and
b) drying the solution or suspension.

References to a carboxyl group and a phosphate group cover such groups in either dissociated or undissociated form. One skilled in the art will appreciate that in general a phosphate group will be in dissociated form, whereas the state of dissociation or otherwise of the carboxyl group will vary according to the pH.

The resulting reagent is useful in conjugation reactions, particularly conjugation with biological molecules (bioconjugation reactions) e.g. for coupling molecules such as proteins to microparticles and for use in preparation of immunogens, as will be discussed in more detail below. The reagent is used by being reconstituted into solution or suspension and brought into contact with either a second reactant or a first reactant (whichever is not present in the reagent). This may be performed in a single step, by adding a solution of the second or first reactant, or in several steps (with the order of steps generally not being important). Suitable reaction conditions, e.g. temperature, pH (with pH preferably being less than 8, less than 7 or less than 6) are provided to enable the conjugation reaction to take place, with the first reactant and second reactant being linked together via an amide bond. Typically, the conjugation reaction will be stopped after a suitable reaction time, e.g. by adding a suitable quencher reagent.

Step b) is preferably carried out reasonably soon after step a), e.g. within about an hour, although this is not necessarily critical.

The carboxyl-activating or phosphate-activating substance (which we will refer to for brevity as activating substance)

and the first or second reactant are preferably mixed in the form of a solution, preferably an aqueous solution.

The solution or suspension is preferably homogeneous.

Activating substances are known in the art, and include carbodiimides, Woodward's reagent K (WRK) and various other materials.

The choice of the activating substance should take account of the type of solvent in the reaction mixture. For reactions in aqueous conditions or in substantially aqueous conditions, an activating substance that is at least partially soluble in water is preferred.

A particularly preferred activating substance suitable for use in the present invention is 1-ethyl-3-(3-dimethylaminopropyl) carbodiimide.HCl (EDC, also referred to as EDAC). Other preferred activating reagents include, for example, N-ethyl-5-phenylisoxazolium-3'-sulfonate (Woodward's reagent K); N-Cyclohexyl-N'-(β-[N-methylmorpholino]ethyl)carbodiimide (CMC); 4-azonia-4,4-dimethylpentyl) carbodiimide (EAC); 2,2-dichloro-5-(2-phenylethyl)-4-(trimethylsilyl)-3-furanone (DPTF) [Murakama et al., Tetrahedrom Letters 37, 7541-7544 (1996)]; and 4-(4,6-dimethoxy-1,3,5-triazin-2-yl)-4-methylmopholinium chloride (DMT-MM) [Kuniishima et al., Tetrahedron 57, 1551-1558 (2001)].

Examples of other activating substances include N,N'-dicyclohexylcarbodiimide (DCC) and N,N'-diisopropylcarbodiimide (DIC); cyanamide; 1,1'-carbonyldiimidazole (CDI); N,N'-disuccinimidyl carbonate (DSC); 1,2-benzisoxazol-3-yl-diphenyl phosphate (BDP); and 2-ethoxy-1-ethoxycarbonyl-1,2-dihydroquinoline (EEDQ). Montalbetti and Falque [Tetrahedron 61, 10827-10852, (2005)] also describe some of these reagents and others that may be used to facilitate the formation of amide bonds from carboxyl and amine containing substances.

Step b) preferably comprises freeze-drying. Suitable protocols are well known in the art. Other possible drying techniques include spray drying, supercritical drying and rotary evaporation.

The method is preferably carried out using a first reactant, i.e. a reactant containing a carboxyl group, for use in a conjugation reaction with an amine-containing second reactant such as a protein, e.g. in a bioconjugation reaction. The reactant may contain one or more carboxyl groups.

The first or second reactant used in the method commonly comprises a label, which provides measurability, but need not do so. Suitable labels are well known and those of particular interest, for example, include coloured or fluorescent microparticles, magnetic microparticles or beads, Quantum dots (Q dots), gold particles, fluorescent dyes, fluorescent proteins, and enzymes. The first or second reactant need not necessarily function as a label, e.g. when the resulting conjugate is to be used as an immunogen for the production of antibodies. Other suitable reactants include nucleic acids and oligonucleotides; carboxylated or aminated dextrans; suitably functionalized beads including agarose and glass; proteins, including antibodies, antibody fragments; glycoproteins, metabolites, analytes, peptides, and other substances or surfaces with carboxyl, amine or phosphate groups, or a combination of these groups.

Microparticles preferably have a protective coating to reduce the likelihood of particle aggregation. The coating conveniently comprises a sugar polymer, e.g. dextran. Suitable coating materials and techniques are well known.

The solution or suspension desirably also includes a polyhydroxylic material, e.g. a sugar, with trehalose being the currently preferred material. This material can act as a stabilizer, particularly in freeze-drying processes, and can also assist in subsequent dissolution of the resulting dried product in use.

The solution or suspension typically includes a buffer. This is not essential, but buffer can assist in stabilizing during a freeze-drying process and can also bring stability benefits in use of the resulting dried product. Suitable buffers include MES, HEPES, MOPS, EPPS (or HEPPS) and CHES. Buffer, if present, is suitably used at a relatively low concentration, preferably 1M or less, more preferably 100 mM or less, yet more preferably 10 mM or less e.g. in the range 1-10 mM.

The pH of the solution or suspension is preferably greater than 4, greater than 6, greater than 7 or greater than 8, and preferably less than 14, more preferably less than 12, and most preferably less than 11.

The solution or suspension optionally includes N-hydroxysuccinimide (NHS) to enhance conjugation reaction efficiency, if required.

The solution or suspension optionally includes detergent, to eliminate possible non-specific or other undesirably binding interactions on use of the resulting dried product.

In a further aspect, the invention provides a reagent produced by the method of the invention.

The invention also provides a dried reagent for use in a conjugation reaction between a first reactant containing a carboxyl group or a phosphate group and a second reactant containing an amine group, comprising a homogeneous mixture of i) a carboxyl-activating or phosphate-activating non-enzymatic substance capable of acting on a carboxyl group or phosphate group-containing moiety to facilitate the formation of an amide bond between a carboxyl group and an amine group or a phosphoramidate bond between a phosphate group and an amine group, and ii) a first reactant or a second reactant.

The reagent preferably includes no NHS.

Other preferred and optional features are as set out above.

The reagent of the invention is preferably in a container such as a vial, conveniently in a suitable quality for use in a conjugation reaction, particularly with a biological molecule, e.g. for use with a sample of 100 ug of antibody to be labelled. Typically, freeze dried mixtures prepared in glass vials with 10 ul, 40 ul, 400 ul or 1 ml of solution or suspension would contain an amount of EDC (based on mol weight of 191.7 for EDC.HCl) of around 2-20 ug, 7.7-77 ug, 77-770 ug, and 192-1920 ug, respectively.

The reagent is preferably made by being dried in situ in the container by the method of the invention, but may alternatively be made in bulk and dispensed into containers e.g. vials.

The invention also provides a conjugation kit, comprising a supply of reagent in accordance with the invention, and instructions for use.

The kit optionally includes a supply of a quencher reagent, e.g. beta-mercaptoethanol.

The kit optionally includes a supply of a buffer, e.g. MES at pH5 or pH6. In use, buffer is preferably added to the reactant to be conjugated, e.g. antibody, which is then added to the reagent of the invention.

The invention also provides a method of performing a conjugation reaction, especially a bioconjugation, the method comprising use of the reagent, or use of the conjugation kit, in accordance with the invention as hereinbefore defined. The steps of the conjugation reaction method typically comprise reconstituting the dried reagent in a suitable liquid (preferably aqueous, such as distilled water or an aqueous buffer solution, or optionally a sterile solution), and contacting the reconstituted reagent with a molecule to be conjugated (e.g. an antibody or the like).

The invention can thus (i) simplify many bioconjugation procedures (ii) eliminate the tedious and wasteful practice of having to prepare fresh solutions of carbodiimide for every experiment, and (iii) provide a clear technical advance over methods involving temporal/spatial separation of reactants.

The present invention is based on work re-examining the stability of EDC in solution under a wide variety of conditions, and resulted in the development of useful starting points for the production of a a multi-component homogeneous freeze-dried mixture containing a carboxyl-activating substance such as EDC.

EDC was subjected to various treatments and residual activity was measured in a protein conjugation assay involving gelation of a concentrated protein solution, or, more directly, by a reaction with an aromatic amine (aniline) to form a measurable guanidine compound. From these experiments we were able to identify a number of conditions in which EDC was surprisingly stable to hydrolysis. Another carboxyl-reactive molecule, Woodward's reagent K (WRK), which too is reported to be unstable in aqueous environments, was also formulated successfully using methods of the present invention.

In our laboratory over a period of months we performed numerous reactions in aqueous media using carbodiimides where we adhered to the accepted guidelines in relation to handling of EDC. Our concern over the possible degradation of powdered EDC stocks, which may be exacerbated by repeated opening and closing of stock bottles routinely stored in freezers at −20° C., prompted us to develop a BSA gelation assay (Example 1) to check the integrity of EDC solutions. However, EDC powder withdrawn from bottles that were old or that appeared to have become damp during repeated use (i.e. showing signs of clumps rather than the fine powder evident on first opening) did not yield solutions in water that were markedly inferior in the BSA gelation assay. This prompted us to test EDC after allowing a solution to 'age' for several hours; the results were certainly not consistent with a rapid rate of hydrolysis and led us to question the validity of some of the statements in the prior art about the stability of EDC.

The finding that EDC could be left standing in water for a significant period of time apparently without dramatic loss of activity raised the question of whether it would also be possible to combine EDC with carboxyl-containing substances and store the mixture, at least for short periods of time, before carrying out reactions with other suitably functionalised molecules. We considered that the preparation of a freeze dried mixture might allow conjugation reactions to be carried out days, weeks, months or even years later. We are aware of no reports of freeze drying of homogeneous multi-component mixtures comprising EDC and carboxyl or amine-containing substances and the use of such a materials in conjugation reactions with other molecules.

Initially, we investigated the stability of EDC when combined with biological buffers or other reagents over a wide range of pH values, and also in the presence of functional groups (e.g. carboxyls) reported to accelerate decomposition of EDC. There is scant information in the literature on reactions between EDC and other molecules in aqueous alkaline buffers. After pre-incubation of EDC in each condition for either 5 min or 24 hours, each EDC/buffer mixture was added to a concentrated solution of BSA in MES buffer at pH 6 and the time required for a gel to form was determined (Example 1).

In this test, an increase in gelling time after a short period of pre-incubation could be caused by rapid hydrolysis of EDC (i.e. reaction with water) or by a fast reaction between EDC and another component in the mixture. Even without loss of EDC in the pre-incubation phase, components in the mixture could still cause interference in the second (gelation) phase of the BSA assay, for example, by attacking EDC specifically at the pH used in the gelling reaction, or by interfering in some other way with the formation of o-acylisourea groups, or with the reaction of those groups with lysine residues on other BSA molecules, which is necessary for intermolecular crosslinking and gelation. Irrespective of the actual mechanism of any interference, the BSA gelation assay is an example of an EDC-mediated bioconjugation reaction and thus allows substances to be identified that one may prefer to exclude from mixtures that are intended to be freeze dried and used for EDC-mediated conjugation of biomolecules.

We found that there was no simple relationship between pH in the pre-incubation phase and gelling time, perhaps because a number of factors operate to influence the outcome in a bioconjugation assay.

After 24 hours of pre-incubation EDC/HCl mixtures failed to cause gelation, in line with expectations based on the reported instability of EDC in acid. Curiously, after 5 minutes of pre-incubation, EDC/100 mM HCl mixtures consistently exhibited the shortest gelling time. We did not investigate this observation further, but it may be explained by the conversion of EDC into a more reactive tautomer.

Several buffer conditions were identified in which EDC activity was only modestly impacted after pre-incubation for 24 hours. Surprisingly, this group included an EDC/acetate mixture at pH 5, a result that was replicated on several occasions, despite a previous report of a half life for EDC of just two minutes in a mixture of 0.1M sodium acetate/0.1M EDC, pH 5 (Jacobson and Fairman, Anal. Biochem. 106, 114-117 [1980]). Less surprisingly, severe interference, irrespective of preincubation time, was noted with polycarboxylic acids (e.g. sodium citrate, EDTA). A number of other buffers including phosphate, carbonate and borate also caused significant interference.

Several mixtures still contained sufficient EDC activity to cause gelation of BSA even after six days of pre-incubation at 25° C.

A number of promising conditions were further evaluated using a more direct test of EDC activity involving the conversion of aniline into phenylguanidine, essentially using the method of Williams et al., (Anal. Biochem. 114, 173-176 [1981]) (Example 2). This assay allowed concentrations of EDC to be measured below the threshold (~20 mM) for causing gelation of BSA and permitted the stability of EDC (either to hydrolysis or to other reactions) to be measured without the requirement for an activated carboxyl group.

A number of buffer formulations were identified in the aniline assay that had little effect on EDC after pre-incubation and/or freeze drying. Moreover, we identified conditions in which EDC could be combined with tri- or tetravalent carboxylic substances (EDTA, citrate) with no evidence of extensive catalytic destruction of EDC.

Overall our findings on the stability of EDC corroborate some of the statements in the prior art but contradict others. Our data clearly shows that EDC is far more stable that is generally recognised and more importantly that it is possible to combine EDC in solution with low molecular weight polycarboxylic substances without substantial loss of EDC. We were therefore encouraged to see if other polyvalent carboxylic substances (e.g. microparticles) could be combined with EDC and freeze dried prior to use in bioconjugation reactions with aminated molecules.

Microparticles are widely exploited in the life sciences, with applications in diagnostic assays for detecting analytes in fluids such as blood or urine (e.g. lateral flow immunochromatographic strip tests and agglutination assays). Fluorescent microparticles and quantum dots are used in flow cytometry to detect populations of cells expressing particular antigens. Magnetic particles have a variety of uses in research laboratories and in diagnostic devices. There are also many other types of microparticles that are constructed from a variety of materials, usually with multiple variants of each type, for example, different sizes, colours, surface functionality, and so on.

For application in biological assays, microparticles must be coated with a substance that can interact with other biomolecules or analytes. The substance is commonly an antigen or an antibody, though a broad range of molecules may be attached to the surface of a microparticle by either non-covalent or covalent means. In the majority of diagnostics applications involving immobilisation of antibodies a passive non-covalent approach to coating is used. Covalent attachment is more commonly employed with small molecules or analytes, and microparticles with a variety of surface functions are available (e.g. carboxyl, amine, aldehyde). Carboxylated or amine surfaces can be covalently coupled with antibodies or analytes using carbodiimides or other functionally equivalent activating substances.

Latex microparticles are hydrophobic and are notoriously prone to aggregation. For passive coating an excess of the binding entity (e.g. antibody) is used so that the entire surface is covered, which reduces the risk of contact between hydrophobic surfaces or of antibodies acting as a bridge between particles causing aggregation.

In some cases the antibody may be mixed with another protein (e.g. BSA) which provides a mechanism for of controlling or adjusting the amount of antibody displayed on the surface of the particle and helps to maintain colloidal stability.

Should any centrifugal wash steps be required to remove excess reagents from a suspension of microparticles the centrifugation steps tend to compact the particles and encourage aggregation. Aggregates once formed are extremely difficult to break up and sonication may be required.

Passive coating is usually carried out at a pH near to the isolelectric point of the coating substance. Thus with antibodies, especially those of the monoclonal variety, the coating process may have to be optimised for each antibody reagent.

Covalent coupling strategies have a number of benefits; the secure attachment of the binding entity to the microparticle potentially allows greater stability, longer shelf life and fewer constraints when developing of assays. For example, detergents which are often employed to reduce non-specific binding in immunoassays may strip passively adsorbed the antibodies from the microparticle and interfere in immunodiagnostic assays.

In the case of carboxyl particles, the amino groups on antibodies react to form a stable amide bond. In the case of aminated particles, the connecting amide bond is reversed but otherwise is equivalent.

The use of an amine-coated particle may be desirable if the analyte only has carboxyl groups available for coupling or if the antibody of interest contains a critical lysine residue in the antigen-binding domain. However, it should also be noted that antibodies may polymerise, especially if present at high concentrations and the critical lysines may still engage is polymerization reactions with other antibody molecules.

Despite the many advantages of covalent conjugation the procedures for carrying out such reactions the procedures are longwinded and the risk of aggregation remains.

Microparticles are also reported to aggregate when frozen (e.g. Polysciences technical datasheet 238; rev #010, active 18 Feb. 2009), providing additional challenges in the development of freeze dried mixtures of EDC with microparticles.

For use in the present invention, primarily because of the tendency of carboxylated microparticles to aggregate in the presence of EDC or after centrifugation, we employed microparticles with a protective dextran coat. Dextrans have been used by others to coat microparticles to give a more hydrophilic surface.

Dextrans were chemically modified to introduce functional groups to allow covalent attachment to the core microparticle and to provide surface functional groups able to participate in conjugation reactions with other molecules.

Functional groups may be engineered into dextrans to suit the chemistry of the particular microparticle of interest. For example, carboxymethyl (CM) groups may be introduced into dextran using bromoacetic acid or chloroacetic acid using methods well known in the art. Such derivatives of dextran may be covalently attached in a carbodiimide-mediated reaction to aminated microparticles.

CM-dextran derivatives may be further reacted with an excess of a low-molecular-weight diamine, such as ethylenediamine, to generate an aminated dextran (AM-dextran) molecules, which can then be attached to carboxylated microparticles.

The density of carboxyl or amine groups on the surface of a dextran molecule may be controlled by varying the amount of haloacetic acid used in the initial carboxylation reaction and/or by controlling the efficiency of subsequent amination reactions.

Amines may also be introduced into dextrans after treatment with periodate, which cleaves cis-diols creating aldehyde groups. The aldehyde groups may be further reacted with diamines to create Schiff bases, which can be stabilised using methods well known in the art.

In the present invention, aminated dextrans are covalently attached to carboxylated microparticles using a carbodiimide. In a preferred embodiment the amines on the dextran coat are then reacted with succinic anhydride to afford a carboxylated surface.

If the number of dextran amines required for efficient coating of microparticles is greater than the number required, or desirable, for subsequent conjugation reactions with other molecules, the number of available amines may be reduced by an incomplete reaction with a blocking agent prior to treatment with succinic anhydride. For example, sulfo-NHS acetate (Bioconjugate Techniques. G T Hermanson 1996; ISBN 0-12-342335-x; p 127) may be used to block amines.

On the other hand, if insufficient amines are available either for the coating step or for subsequent conjugation reactions the CM-dextran may be reacted not with a diamine but instead with a low molecular weight triamine or polyamine to provide additional amine functionality.

The methods of the present invention are not limited to any particular coating method and may be applied to microparticles either with or without a dextran coat. Moreover the microparticle may be coated with one layer or multiple layers of dextran.

A primary aim of the dextran coat is to prevent aggregation of the particles and in this regard a dextran with a high average molecular size is preferred, as large size generally seems to be more effective maintaining colloidal stability.

In a preferred embodiment of the present invention EDC or other carboxyl-activating substance is combined with latex particles, preferably coated with a protective polymer such as dextran. The protective layer bears a plurality of either amine groups or carboxyl groups and the microparticles may be combined with EDC or another suitable carbodiimide in a suitable buffer, with other additives, and the resulting homogenous mixture is dispensed into small vials and frozen prior to freeze drying and subsequent application in conjugation reactions.

Vials produced in this way may be assembled in the form of a convenient one-step conjugation kit, in which a reaction between the biomolecule of interest and the microparticle may be initiated simply by reconstituting the freeze dried mixture with a solution of the biomolecule.

In the application of such a kit to bioconjugation reactions one needs to give careful consideration to the amount of carbodiimide in the freeze-dried mixture, both in absolute terms and with respect to other entities in the mixture; and with respect to other entities (e.g. nucleophiles added in the form of a solution) that might be introduced later on. One also has to consider whether the volume of liquid to be introduced is greater or less than the original volume (i.e. prior to freeze drying) of EDC-containing solution, in order to anticipate the concentration of each component in the final reaction mixture.

One must also consider the possibility of there being components in the entity used for dissolution of the freeze dried mixture which may alter the efficiency or rate of the EDC or other carboxyl-activating substance-mediated reaction. For example, many laboratories perform conjugation reactions to link antibodies to carboxylic surfaces, or to other carboxyl-containing biomolecules, and commercially available antibodies often contain substances (e.g. tris, phosphate buffer) that are reported to interfere with the action of carbodimides. These potential difficulties may be addressed in one of several ways.

First, the antibody can be desalted or dialysed to provide a more favourable buffer formulation. Such manipulations are commonly employed with volumes of around 0.1 ml or above. With much larger volumes other techniques such as cross-flow filtration may be used. It may be possible to remove some unwanted substances using particulate scavenging materials; for example, mixed-bed ion exchangers have been used to remove unwanted ionic components from protein solutions.

Second, a series of freeze dried compositions could be produced to accommodate the variable formulations of antibodies (or of other entities) that might be encountered in conjugation reactions. For example, antibodies with a preferred buffer formulation might require a relatively small quantity of EDC etc to effect conjugation. By contrast, antibodies formulated with substances known to accelerate the decomposition of EDC etc (e.g. phosphate) might be added to a polycarboxylic acid substance (e.g. a latex bead) freeze dried with a higher content of carbodiimide.

Third, a single freeze-dried formulation with a relatively high amount of EDC etc might be produced. Such a mixture, even if contacted with an antibody with an unfavourable formulation, may still allow the reaction to go to completion in a reasonable period of time. Opinion as to what period of time is reasonable may vary among laboratory operators, but a reaction time of one hour would not be unusual. If the same antibody were then presented in a preferred buffer formulation the reaction would likely be faster and may progress to the required end point within a matter of minutes, in which case, to limit potential damage from over-exposure to EDC etc the reaction could be quenched using a suitable method.

Fourth, 'pH modifiers' may be added to the antibody prior to being contacted with the freeze dried mixture in order to move the final reaction pH up or down, thus altering the rate of the carbodiimide-mediated reaction. The sensitivity of the particular antibody or biomolecule under study to pH will impose a limit on range in which the pH can usefully be varied. In this approach, the buffering capacity of the freeze dried mixture ideally is relatively low to facilitate adjustment of the pH by addition of only modest amounts of modifier. Any further change of pH, as may be required later on, for example, as part of a quenching procedure, is also easier to accomplish if one begins with a buffering system of relatively low capacity.

Modifiers may also be exploited to optimise the extent of reactions of amines of varying pKa. In the case of freeze dried mixtures comprising a carbodiimide and a polycarboxylic substance, both two-step and one-step reactions with amines are possible, just as with traditional EDC conjugation methods using freshly prepared solutions. For example, in a two-step approach the pH of the freeze-dried mixture may initially be reduced via addition of a low pH buffer to favour the formation of the o-acylisourea. After a suitable period of time, the aminated molecule is introduced in or with a buffer of higher pH to shift the reaction pH upwards thus increasing the proportion of amines in the more reactive unprotonated state, thus facilitating amide bond formation.

For many amines, especially biomolecules (e.g. proteins) with a plurality of amine functions (principally from lysine side chains) with a range of pKa values because of the influence of the microenvironment in which each lysyl residue is situated, the simplest approach is the one-step reaction in which the freeze-dried carboxylic substance/EDC mixture is reconstituted with a buffered solution of the amine-containing biomolecule.

N-hydroxysuccinimide (NHS) may optionally also be added to the reaction mixture either prior to freeze drying or along with solutions used for dissolution of the freeze-dried mixture. NHS may be useful if the efficiency is otherwise too low. Equally, one can also envisage situations in which substances that cause interference, such as phosphate, may be deliberately introduced to decelerate reactions that are otherwise too fast.

The rate or efficiency of reaction may also be varied by altering the concentration of reactants. For example, reconstitution of the freeze dried mixture with a fixed amount of antibody provided in two volumes, 'x' and '5x' will result in a five-fold difference in the concentration of microparticles, EDC etc, antibody, and any other components. In the case of reaction volume 'x' the rate of reaction may be much faster than for volume '5x'. Thus it may be possible or desirable to use less EDC etc in freeze dried mixtures if the dissolution in a relatively small volume is planned.

It will be evident from the above discussion that even with freeze-dried mixture of fixed composition there are very simple strategies for varying the efficiency of conjugation reactions.

It will also be evident from the above discussion that the methods of the present invention allow an almost infinite number of freeze-dried formulations to be prepared quickly and easily, simply by mixing solutions of the various components in different proportions.

In a preferred embodiment of the invention the pH of the final mixture of components prior to freeze drying is in the range pH 1 to 14.

The preferred buffers for stabilizing EDC are MES, pH 6.0; HEPES, pH 7.5; MOPS, pH 7.5; EPPS, pH 8.5; EPPS pH 9.0, CHES, pH 9.2.

WRK was stabilised in all of the buffers examined: MES buffers at pH 5, pH 6, and EPPS pH 8.5. For conjugation reactions however, WRK showed highest efficiency at pH 5.

Preferably the pH of the buffered solution is within 5 pH units of the pKa of any buffering substance used to maintain pH, more preferably within 2.0 pH units, even more preferably within 1 pH unit.

In freeze drying processes it is generally accepted that the concentration of buffers and salts should be as low as possible and it is noteworthy that EDC was most stable in water (Example 1).

Any buffer in the mixture is there simply to achieve effective control of pH during the preparation and freeze drying of multi-component mixtures, wherein the said components may have a tendency to move the pH, either in solution or during the freeze drying process itself, to one that is less desirable, i.e. in which unwanted reactions take place.

Preferably, any buffering substance that is employed is present at a relatively low concentration, preferably 1M or less, more preferably 100 mM or less, even more preferably 10 mM or less.

It will be obvious that it may be possible to use in the present invention the same buffers at pH values slightly different from those referred to above, or to use other buffers that essentially have the same buffering function.

It is convenient in the present invention to add buffers to mixtures that are to be freeze dried using 10×, 50× or 100× buffer concentrates. One should be aware that dilution of concentrated stocks may lead to a significant change of pH. Thus if it is necessary to achieve a particular final pH one should factor any change expected from the dilution effect, and also influence of other components in the mixture.

Mixtures of microparticles and carboxyl-activating substance optionally contain a polyhydroxylic substance.

The hydroxylic substance preferably is a sugar; of which many examples are known in the prior art. Many sugars have been used as stabilisers in freeze drying processes.

In a particularly preferred embodiment the sugar is trehalose.

While proteins such as antibodies contain an abundance of both amines and carboxyl functions, EDC is widely employed to attach such molecules to particles or other surfaces. There is clearly a risk of self-polymerisation in such situations which could alter and/or damage the biological activity of the antibody; the risk increases with increasing concentration of antibody or EDC.

One strategy that could potentially be used to enhance conjugation efficiency is to use lower concentrations of antibody and draw the antibody into close proximity with the target molecule (e.g. particle, surface) prior to addition of carbodimide.

In a preferred embodiment of the present invention the ionic strength of the buffer used in the conjugation reaction between a dextran-coated particle and entity is relatively low to promote initial non-covalent electrostatic interaction of the molecules to be conjugated. The proximity of protonated amines on the antibody with carboxyls on the microparticle permits an efficient reaction at relatively low concentrations of EDC. The use of low concentrations of EDC also reduces the amount of quencher required to stop the reaction.

Where solutions of low ionic strength cannot easily be employed, the reaction efficiency may be enhanced by using more carboxyl-activating substance e.g. EDC or a lower pH (potentially increasing the reactivity of EDC) in the range 7 to 4 and increasing the positive charge on the antibody which may facilitate non-covalent interactions with negatively charged surfaces.

Microparticles may be further processed after the conjugation reaction using methods well known in the art to change the formulation of the buffer as required by the intended application and to remove excess reactants or by-products. Depending on properties and size of the microparticles, and depending on the size of the molecules to be removed, processes such as desalting, dialysis or centrifugation/washing may be employed. Desalting is satisfactory if only small molecules are to be removed. Dialysis may be applied to a wider range of sizes of molecules, subject to selection of a dialysis membrane with an appropriate molecular weight cut-off.

The conjugation reaction itself and/or buffer used to wash away excess reactants from the particles may contain a detergent to eliminate non-specific or other undesirable binding interactions; for example, to remove antibody non-covalently associated with microparticles or to reduce interactions of conjugated microparticles with materials used in lateral flow devices.

The detergent conveniently may be introduced with the carboxyl-activating substance prior to, drying e.g. freeze drying of the particles, or with the antibody used for dissolution of the freeze dried mixture, or after the conjugation reaction has either ended or has been terminated by addition of a quencher. Introduction of the detergent along with the antibody or after conjugation provides the greatest flexibility, since it allows the composition of the reaction mixture or of the final conjugate to be varied at will to suit each experimental objective.

Where uncoated particles are combined with carboxyl-activating substance, the conditions that are employed preferably do not allow a reaction with substance, as this may encourage aggregation of the particles prior to freeze drying. The conditions may be adjusted after freeze drying, by addition of a nucleophile in a suitably buffered solution, to provide the appropriate conditions for an activating substance-mediated reaction.

The methods of the present invention can also be employed with gold particles, which have applications in light microscopy, transmission electron microscopy, scanning electron microscopy, Western blotting and lateral flow. Gold particles are available commercially in a range of sizes; most commonly spherical particles are used in biological applications. The diameter that is best for each application varies.

As with latex microparticles, gold particles readily aggregate and methods used to attach antibodies are laborious, often requiring extensive trials over a range of protein concentrations and pH values to achieve a stable conjugate. The mechanism of binding is incompletely understood but successful outcomes are more likely if the pH is adjusted to a value that is slightly higher than the pI of the protein to be coated. Gold may also interact with sulphur atoms in proteins (found in cysteine and methionine residues) by means of a dative bond.

In the present invention, gold particles are coated preferably with dextran with both amino and thiol functions, which affords multi-point attachment of the coating substance. The coated particle is then treated with succinic anhydride to afford a carboxylated surface for use in subsequent conjugation reactions.

Thiolated dextrans may be prepared using one of several methods well known in the art. In a preferred embodiment, CM dextran is reacted with a mixture of two diamines, ethylene diamine and cystamine, in the presence of EDC. The modified dextran is then reduced with DTT and desalted to remove excess reducing agent. The ratio of amine:thiol on the surface of the dextran may be adjusted by varying the ratio of the two diamines. Preferably, the molar ratio is 80:20 for ethylene diamine:cystamine. This does not necessarily result in the same ratio of amine:thiol functions; typically, the ratio of these functions is approximately 90:10.

Thiol groups may also be introduced into aminated molecules, such as amino-dextrans, by converting a proportion of the amine functions using methods well known in the art.

The thiolated dextran is incubated with gold particles to allow the coat to attach via formation of dative bonds with thiol groups. Other modes of interaction may also occur but a detailed knowledge of these interactions is not necessary to apply the methods of the present invention. Colloidal stability was found to be greatest with dextrans of relatively large size. Aggregation was apparent with aminated dextrans of 40 kDa size or below.

In a preferred embodiment thiolated dextran of around 150 kDa-500 kDa is preferred for coating of 40 nm gold particles.

After coating, the gold particles are preferably treated with an excess of succinic anhydride to afford coated particles with high colloidal stability which can be contacted with EDC and freeze dried using methods of the present invention.

In a preferred embodiment coated gold particles in MOPS buffer pH 7.2 are mixed with trehalose and EDC prior to freeze drying.

Quantum dots (Q dots) can also be conjugated to other molecules using methods of the present invention. Q dots are brightly fluorescent inorganic semiconductor nanoparticles with a number of advantages over organic dyes and fluorescent proteins for cell and tissue imaging. The core of Q dots typically is made up of cadmium selenide (CdSe), which is coated with zinc selenide to reduce photochemical bleaching and to increase quantum yield. Often the emission properties of Q dots are dependent on the size of the particle, thus Q dots can be tuned to particular parts of the spectrum by careful control of size during the manufacturing process, but with other types of Q dots the fluorescence properties can be changed by altering the composition while maintaining a fixed size.

Q dots are usually very hydrophobic but they can be made compatible with biological applications by, for example, encapsulation in an amphiphilic polymer. As with other type of particles, Q dots may be obtained from commercial sources with a variety of functional groups.

We found Q dots had a tendency to aggregate even with an amphilic polymer surface and in the present invention carboxylated Q dots are preferably coated with aminated dextran to enhance colloidal stability. The stabilising effect was seen primarily with dextrans of relatively large size, preferably larger than 40 kDa, preferably 150 kDa or more.

In a particularly preferred embodiment EDC-mediating coating reaction was performed with 150 kDa AM-Dextran in MOPS buffer, pH 7.2.

After succinylation, coated Q dots in a suitable buffer were mixed with trehalose and EDC and freeze dried.

Aside from their use in coupling molecules to microparticles, carbodiimides are also used in the preparation of immunogens. For example, EDC may be used to mediate crosslinking of amine- or carboxyl-containing analytes to 'carrier' proteins such as KLH (keyhole limpet hemocyanin) or BSA (bovine serum albumin). Carrier proteins often have both carboxyl and amine functions which can lead to homopolymerisation in the presence of carboxyl-activating substances, though polymerization is not necessarily detrimental, and may even be beneficial if the conjugate if it is to be used the purpose of eliciting the formation of antibodies in a host animal. However, there must be sufficient conjugation of the analyte with the carrier protein so that the carrier is decorated with analyte molecules on its surface.

Cationized carrier proteins are often advocated for the production of immunogens as this elicits a stronger immune response. In this situation the likelihood of homopolymerisation during freeze drying is reduced, but the analyte must contain carboxyl functions. Direct reaction of amines with arboxyl-activating substances such as EDC to generate guanidines may be an unwanted side reaction in this situation.

BSA was cationized with ethylene diamine and freeze dried in the presence or absence of EDC in an alkaline buffer. The freeze dried material was reacted with carboxyfluorescein to see if the carboxyl functions could react with aminated BSA after exposure of cationised BSA to EDC prior to and during a freeze drying cycle. A significant reaction in the presence but not absence of EDC observed.

In a preferred embodiment of the present invention, carrier proteins are cationised and freeze dried in the presence of EDC in a slightly alkaline buffer.

The methods of the present invention may also be used with low molecular weight molecules, which can be contacted with carboxyl-activating substance and dried. Subsequent dissolution of the mixture with a suitably funtionalised molecule may be used to initiate a conjugation reaction.

For example, carboxyfluorescein may be contacted with a sugar and EDC at alkaline pH and freeze dried. The material may be reconstituted with an aminated molecule at a suitable pH.

A similar approach may be used with a small molecule bearing amine or hydrazide groups which, after freeze drying, may be conjugated to carboxylic substances.

To determine conditions that minimize self polymerization of substances (e.g proteins) containing both amine and carboxyl functions one can use SDS-PAGE analysis to detect the presence of dimers, trimers and higher polymers. The subset of buffers identified in this initial screen can then be examined under the conditions of freeze drying.

In the present invention, using EDC and unmodified BSA in a variety of buffers we found that there was minimal reaction with the following buffers: EPPS pH 8.5; CHES pH 9.3. Polymerisation at lower pH values with HEPES and MOPS were detectable and extensive crosslinking occurred with MES buffers at pH 5 or pH 6.

Thus in a preferred embodiment of the present invention, protein molecules containing both carboxyl and amine groups may be contacted and freeze dried with EDC in a buffer of >pH 7 and preferably >pH 8. Subsequent reaction with amine- or carboxyl-containing small molecules in an acidic buffer may be carried out. Preferably the small molecule is in excess to prevent or minimise self-polymerisation of the protein.

Regardless of the specific EDC-mediated reaction under study, in any bioconjugation experiment a method to terminate the reaction must be established. The methods available to stop reactions of the present invention are identical to those for other EDC conjugation procedures.

Reactions performed according to methods of present invention may be quenched by dilution of the reaction mixture, or addition of substances capable of deactivating EDC, or of interfering in other ways with conjugation reactions, or a combination of these approaches.

Physical separation of excess EDC and by-products may be achieved quickly and easily by desalting, especially if the product of the conjugation reaction is a large molecule greater in diameter than the pores of a desalting chromatography matrix.

Substances that interfere in carbodiimide reactions are also known. For example, thiols deactivate carbodiimides and may be used at concentrations that are compatible with biomolecules in the reaction mix. Very high concentrations of thiols may be contraindicated in the case of antibody molecules or other molecules with disulfide bridges, whose integrity may be required for maintaining correct structure and biological function.

Carboxyls are known to accelerate the hydrolytic decomposition of carbodiimides via the o-acylisourea intermediate and may if present in excess compete with carboxyls on any biomolecules in the conjugation reaction for the limited amount of carbodiimides. One should consider with this approach the possibility that the o-acylisourea derivative generated from the quencher may also react with amines attached to biomolecules in the conjugation mixture. Capping of amines in this manner may not be suitable in all situations.

Similarly, amines in sufficiently high concentration could be used to attack EDC, but the possibility again of attaching the quencher molecule to o-acylisourea moieties generated on the conjugate has to be considered.

Hydroxylamine had also been reported to interfere with EDC-mediated reactions and may also be used as quenching agent.

Although reactions in phosphate buffers are often recommend with EDC, there is overwhelming evidence that phosphate reduces reaction efficiency. Addition of phosphate buffer at the end of the conjugation reaction may be desirable especially if other types of quenching agents are contraindicated.

Whatever type of quencher is used the most desirable concentration will be determined from a consideration of the initial concentration of EDC, the time that is allowed for the quenching step, the intended application of the conjugate and the types of molecules involved in the conjugation reaction.

For one step methods in which excess EDC is not physically separated from the conjugate, direct deactivation of EDC is the method of choice. In a particularly preferred embodiment beta-mercaptoethanol is the quenching agent and is introduced in a buffer of pH>7, preferably around pH 8. The buffer may be, for example, TBS or PBS.

Finally, the methods of the present invention have been applied to different types of coated microparticles, including latex microparticles, gold microparticles and Q dots. Biomolecules and small organic molecules have also been freeze dried with EDC and used in conjugation reactions. The methods may also be applied to an alternative carboxyl activating agent, WRK. The minimum size of dextran required to coat each type of particle may vary, but it is obvious from the methods described herein that a range of sizes of dextran should be evaluated as a first step with any new type of particle. It will also be obvious that numerous variations in the composition of freeze dried mixtures may be made without departing from the spirit and scope of the present invention, which is exemplified more fully below.

The invention will be fully described, by way of illustration in the following Examples and with reference to the accompanying Figures, in which.

Figure 3:
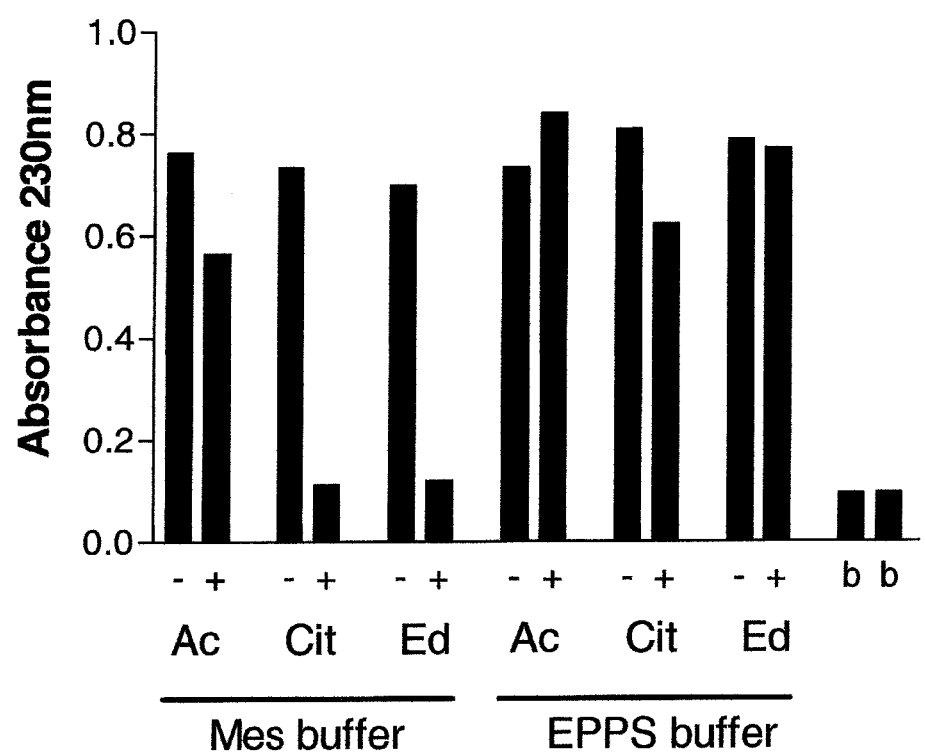
Figure 4:
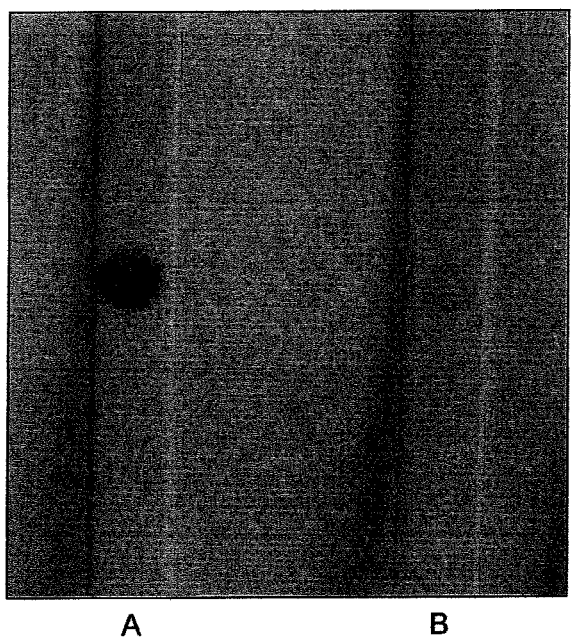
Figure 5:
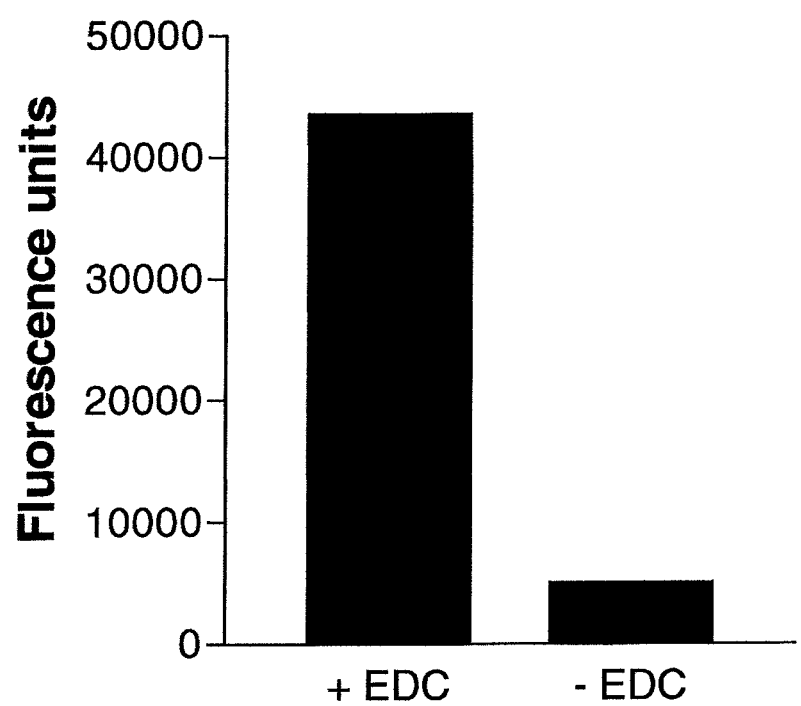
Figure 6:
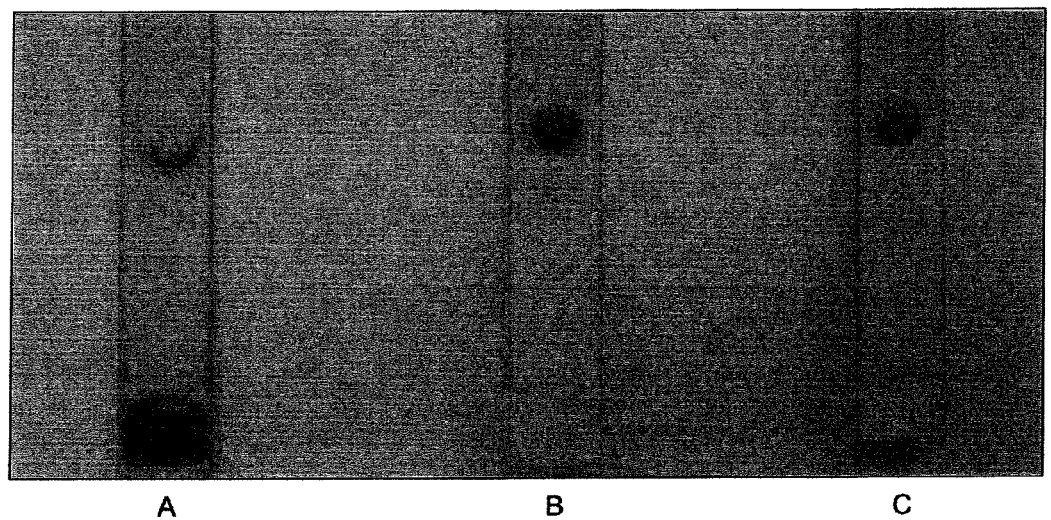
Figure 7:
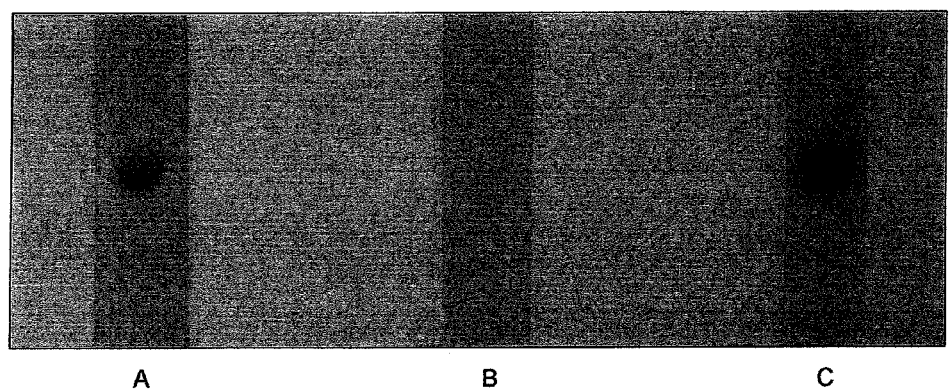

FIG. 3 shows the stability of EDC as measured by reaction with aniline after incubation in either MES buffer pH 6 or EPPS buffer pH 8.5 in the presence of various carboxylated molecules. Ac, sodium acetate; Cit, trisodium citrate; Ed, EDTA. b, assay blanks (Example 2);

FIG. 4 shows a typical lateral flow test with succinylated dextran coated microparticles freeze dried in the presence (A) or absence (B) of EDC and reacted with goat anti rabbit IgG before testing on a strip spotted with rabbit IgG (Example 8);

FIG. 5 shows fluorescence readings for rabbit IgG-spotted lateral flow strips run with goat-anti-rabbit IgG Q dot conjugates. Conjugates were prepared by addition of a solution of goat anti-rabbit IgG to a freeze dried succinylated dextran-coated Q dot/EDC mixture (Example 10);

FIG. 6 shows lateral flow tests with succinylated dextran coated microparticles reacted with varying concentrations of Woodward's reagent K and goat anti-rabbit IgG before testing on a strip spotted with rabbit IgG. A, 100 mM WRK; B, 10 mM WRK; C, 1 mM WRK (Example 11); and FIG. 7 shows lateral flow tests with succinylated dextran coated microparticles reacted with 10 mM Woodward's reagent K and goat anti rabbit IgG in different buffers before testing on a strip spotted with rabbit IgG. A MES buffer, pH 6; B, MOPS buffer, pH 7.0; MES buffer, pH 5 (Example 12).

EXAMPLE 1

BSA Conjugation Assay

BSA was prepared at 100 mg/ml concentration in 0.5M MES pH 6.0. Samples of EDC (Fluka, product code 03449) in water (1M) were mixed with various test buffers or solutions (each 100 mM) in a 1:1 ratio. The EDC/buffer mixtures were pre-incubated at 25° C. and 100 ul aliquots were withdrawn at different time points and added to 0.4 ml BSA solution, giving a final EDC concentration (assuming no decomposition during the incubation phase) of 100 mM. Tubes were inverted approximately every 10 seconds and the time taken for a gel to form (i.e. the point at which there was no movement of fluid upon inversion) was determined in each case.

Figure 1A:
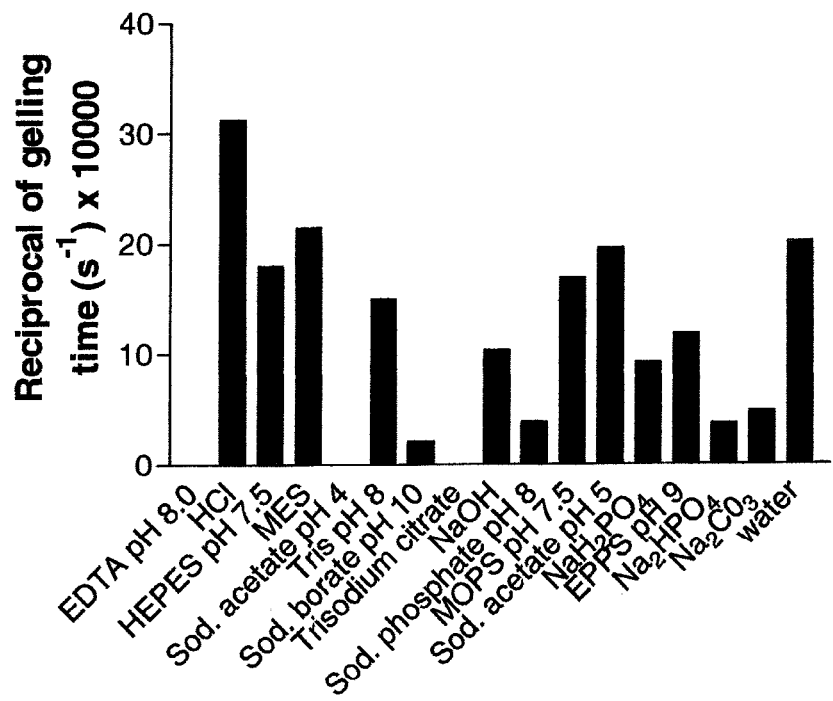
FIG. 1 shows the stability of EDC as measured in a bioconjugation assay (BSA gelation) after pre-incubation of EDC under a variety of buffer conditions for either 5 min (A) or 24 hours (B) (Example 1)
Figure 1B:
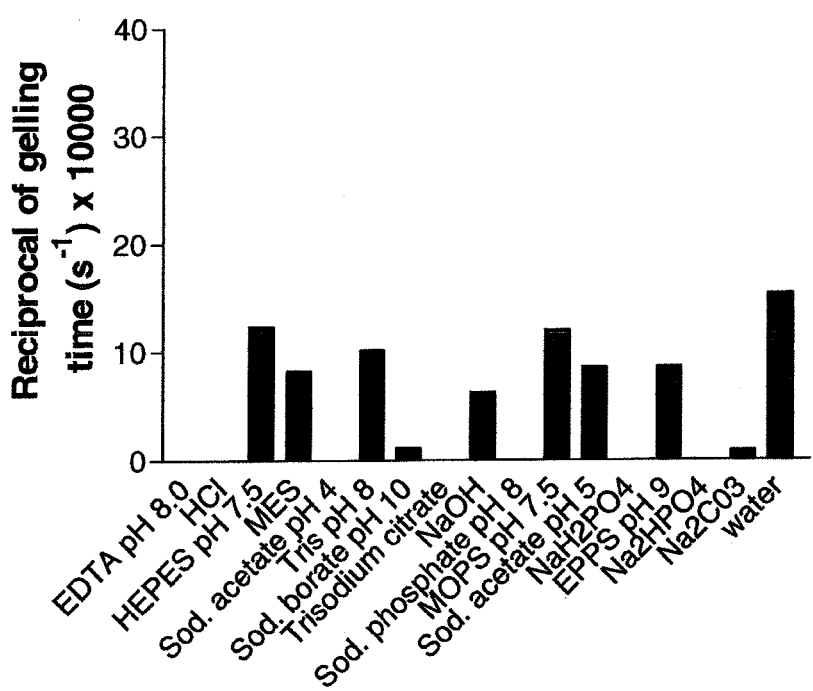

The results are shown in FIG. 1A and FIG. 1B after pre-incubation times of 5 minutes and 24 hours, respectively. Note: reciprocal values have been plotted so that the shortest gelling time corresponds to the bar with the greatest height. No gelation was seen after 5 min of pre-incubation with EDTA pH 8, sodium acetate pH 4, or trisodium citrate. A significant delay in gelation was seen after pre-incubation with phosphate buffer (at alkaline pH), borate and sodium carbonate. Pre-incubation with HCl for 5 min resulted in the quickest gelation reaction, but the sample failed to cause gelation after 24 hours of pre-incubation. Even after 6 days of pre-incubation (data not shown) six samples (water, MOPS, EPPS, Tris, Hepes, NaOH) were still able to cause gelation of BSA.

The relationship between gelling time and concentration of freshly prepared EDC was examined (concentration, time for gelation [min.secs]): 100 mM, 6.59; 90 mM, 8.12; 80 mM, 9.18; 70 mM, 11.20; 60 mM, 13.21; 50 mM, 16.12; 40 mM, 22.47; 30 mM, 50.14; 20 mM and 10 mM; no gelation. Thus even after 6 days of pre-incubation some EDC mixtures show less than 80% decomposition. In the best case (water/EDC)

the observed gelation time of <20 min corresponds to a level of decomposition of less than 60%.

EXAMPLE 2

Aniline Assay

The aniline assay was performed essentially as described by Williams et al. (Anal. Biochem. 114, 173-176 [1981]) with minor modification. A sample containing EDC (100 ul) was added to 100 ul of aniline hydrochloride (1M) and incubated for 1 min at 25° C. A 50 ul aliquot of the mixture was added to 1.20 ml of 2M HCl and the absorbance was read at 230 nm versus control (without EDC).

Figure 2:
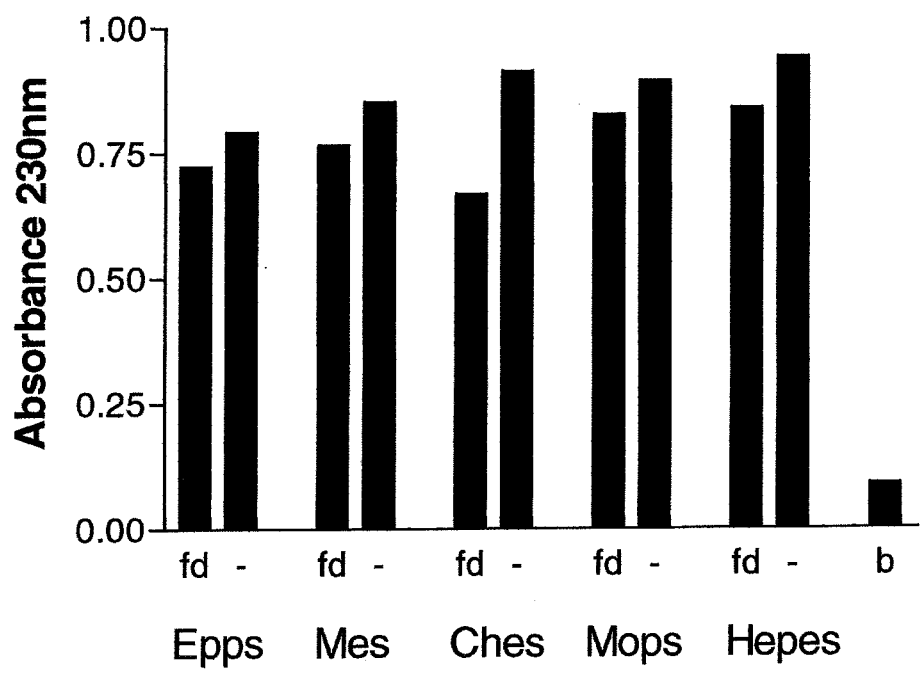
FIG. 2 shows the stability of EDC as measured by reaction with aniline after incubation with various buffers. Fd means that samples were freeze dried prior to testing in the assay. (−) means that samples were not freeze dried. (b) assay blank (mean of 5 samples) (Example 2)

The stability of EDC (10 mM final) was examined in selected buffers (10 mM final, prepared from the following stocks: 1M MOPS, pH 7.2; 1M Hepes, pH 7.5; 0.5M EPPS pH 8.5; 0.5M MES, pH 6; 0.5M CHES pH 9.3). Little or no loss of activity was observed after a three hour period of incubation (data not shown). The suitability of these buffers for freeze drying with EDC was then examined. Materials freeze dried as described in Example 6 were reconstituted in water and tested in the aniline assay. Significant loss of activity was seen with the CHES/EDC mixture, but the other mixtures exhibited only a modest loss of activity (FIG. 2).

The effects of some substances (acetate, citrate, EDTA) reported to catalyse the decomposition of EDC were investigated in 100 mM MES buffer pH 6 and 100 mM EPPS pH 8.5. The buffer/catalyst mixtures were prepared and the pH values adjusted to the stated values prior to the addition of EDC. Some loss of activity was seen in MES buffer after three hours of incubation with acetate (monocarboxyl), citrate (tricarboxyl) or EDTA (tetracarboxyl). The magnitude of the loss was much greater with poly carboxylic acid catalysts. In EPPS buffer the loss of activity was much less pronounced (FIG. 3).

EXAMPLE 3

Preparation of AM-Dextran

Dextran (final concentration 100 mg/ml) was converted into CM (carboxymethyl) dextran by reaction with 1M bromoacetic acid in 2M NaOH. After 48 hours at 25° C. the solution was neutralised to pH ~7.5 by careful addition of small aliquots of concentrated HCl. CM-Dextran was separated from excess reactants and by-products by desalting 1.5 ml portions on Sephadex G25 (PD10 columns, GE Biosciences) equilibrated with 50 mM MES pH 6.0. CM-Dextran was eluted in a volume of 2 ml, to which was added 400 ul of 2M stock of ethylenediamine in 0.5M MES pH 6.0. EDC was added from 1M stock to a final concentration of 100 mM and the mixture was incubated overnight at 25° C. A further addition of EDC to 100 mM concentration was made and the incubation repeated as above. The AM-Dextran mixture was desalted in 1 ml portions on Sephadex G25 into 50 mM MES pH 6.0 to give a final concentration of ~25 mg/ml. This procedure was used with dextran polymers of average size 500 kDa, 150 kDa, 40 kDa (Pharmacosmos product codes 5510 0500 4006, 5510 0150 4006, 5510 0040 4006).

EXAMPLE 4

Coating of Latex Particles with AM-Dextran

Blue latex microspheres (270 nm diameter; parking area 61, Seradyn, product code 83100670020350) (1 ml) were coated by dilution into 4 ml of 150 kDa AM-Dextran (Example 3). After incubation for 30 minutes at 25° C., EDC was added to a final concentration of 100 mM and the microparticles were agitated gently for 24 hours at 25° C.

EXAMPLE 5

Production of Succinylated Microparticles

Dextran coated particles produced as described in Example 4 were supplemented with 400 mM Hepes buffer from 2M stock, pH 7.5, and succinic anhydride (1M in DMSO) was added to a final concentration of 100 mM. The reaction mixture was gently stirred and held between pH 6 and pH 7 by periodic addition of small aliquots of 5M NaOH. Once the pH had stabilised (usually after about 10 mins) the suspension was transferred to a cellulose ester dialysis bag (1 million Dalton cut-off; Spectrum, product code 131486) and dialysed extensively against 25 mM MES pH 6.0. Dilutions of each batch were calibrated in the lateral flow assay and the bulk material was diluted to a suitable working concentration with 25 mM MES buffer.

EXAMPLE 6

Freeze Drying of Dextran-Coated Latex Microparticles

The same basic procedure was used with a variety of dextran-coated latex microparticles prepared as described in Examples 4 and 5. The microparticles were first buffer exchanged by either desalting or dialysis into a buffer of 1-10 mM concentration. Alternatively, buffer concentrate (at least 0.5M) would be added to microparticles suspended in water to give the required final buffer concentration. Types of buffers used included: EPPS, pH 9, EPPS pH 8.5, MOPS pH 7.2, MOPS pH 7, Hepes, pH 7.0, MES pH 6 and MES pH 5. A 0.8 ml portion of buffered coated microparticle solution was supplemented with 100 ul of trehalose stock (1 g dissolved in 2 ml of water) and 100 ul of EDC stock (range 0-100 mM, depending on the required final concentration). In most cases the final concentration was 1, 5 or 10 mM. The volumes were scaled up or down as required to furnish the required amount of material for freeze drying. The microparticles were mixed and dispensed in 50 ul or 100 ul portions, frozen in liquid nitrogen and freeze dried according to the following program in a Virtis Advantage freeze dryer: Step 1, temperature −40° C., duration 1320 min; Step 2, temperature −10° C., duration 60 min; Step 3, temperature +20° C., duration 60 min. These tubes provided sufficient material to run 1 or 2 lateral flow tests. Scale up was achieved by freeze drying greater volumes or by using more concentrated microparticles (Example 20).

EXAMPLE 7

Production and Use of Lateral Flow Strips

Nitrocellulose membranes (approx 4 cm×0.4 cm) were spotted about one-third distance along the strip with 0.5 ul of purified rabbit IgG (2 mg/ml) in 150 mM NaCl plus 5% methanol. Strips were allowed to dry at room temperature for at least 60 minutes, but usually for 2-24 hours, and then blocked for 30 min with 0.1% BSA in either TBS, pH 8, or 50 mM sodium phosphate, pH 7.2. Strips were washed with 0.5% trehalose in water and allowed to air dry. In order to test microparticles coated with goat anti-rabbit IgG, the end of the strip closest to the position of the spotted rabbit IgG was dipped into 50 ul of microparticle suspension; a pad of absorbent paper was applied to the other end. The strip was allowed to run until the entire sample had passed into the nitrocellulose membrane. In some cases the background was cleared by transferring the strip to 50 ul of buffer for a further 4-5 minutes. The buffer could be varied and specific buffer conditions are given elsewhere.

EXAMPLE 8

Reaction of Freeze Dried Microparticles with Antibodies

Freeze dried microparticles were reconstituted with a solution containing goat anti-rabbit IgG (1-50 ug) in MES buffer (50-200 mM) pH 6 in a final volume of 50 ul. After incubating for a suitable period of time (2.5 min up to 1 hour), samples were quenched by dilution with 1 ml TBS pH 8.0. The samples were centrifuged for 15 minutes at 18000×g. The supernatant was carefully discarded and the pellet for resuspended in 50 ul of TBS containing 0.1% Tween 20. FIG. 4 shows a typical example obtained with blue latex 270 nm dextran-coated succinylated microparticles freeze dried in 10 mM EPPS buffer, pH 8.5, in the presence or absence of 10 mM EDC.

EXAMPLE 9

Q Dot Conjugation Reactions

Q dots (Crystalplex 20 nm, product code NCC-665, carboxylated nanoclusters, emission max 665 nm; 28 mg/ml) were diluted 1/10 in 50 mM MOPS pH 7.0 and 100 ul of suspension was combined with 400 ul of 150 kDa AM-dextran (Example 3) in 50 mM MOPS pH 7.0 and incubated on a Spiramix for 30 min at 25° C. EDC (26 ul) was added from 2M stock to give 100 mM final concentration. After 5-16 hours of incubation, 80 ul of 1M succinic anhydride in DMSO was added to the suspension, along with 160 ul of 2M HEPES/10 mM EDTA, pH 7.5 and 40 ul of 50 mM MOPS pH 7.0. After 30 min of incubation on a Spiramix the sample was desalted on a PD10 column equilibrated with water. The succinylated nanoclusters were spun in a microfuge for 15 min at 12000 rpm and the pellet was resuspended in 400 ul of water.

EXAMPLE 10

Reactions of Q Dots Freeze Dried in the Presence of EDC

Portions of Q dot suspension (50 ul) prepared as described in Example 9 were mixed with 5 ul of trehalose stock (1 g+2 ml water), 2.5 ul of 200 mM EPPS, pH 8.5, and 3 ul of either 100 mM EDC (final concentration 5 mM) or water. Samples were frozen and freeze dried using the protocol outlined in Example 6, and then stored at −20° C. for 2 days. A mixture containing goat anti-rabbit IgG (13 ul of 2.3 mg/ml), 60 ul of 0.5M MOPS, pH 7.0, and 77 ul of water was prepared and a 50 ul portion (10 ug of antibody) was added to each tube of freeze dried Q dots. Conjugation and washing was carried out as described in Example 8. Lateral flow tests were carried out as described in Example 7. The background was cleared by running 50 ul of buffer up the strip and the area corresponding to the region of immobilised rabbit IgG was excised and read (excitation 350 nm/emission 665 nm) in a black 96-well plate in 50 ul TBS. For conjugates prepared either with or without EDC the fluorescence readings were 43552 and 5034, respectively, as shown in FIG. 5.

EXAMPLE 11

Optimising the Concentration of Woodward's Reagent K

Dextran coated microparticles (200 ul) (prepared as described in Example 4) were desalted into 350 ul of water using a NAP-5 column. Stocks of Woodward's reagent K (WRK) were prepared at 1M, 100 mM and 10 mM in water. 40 ul of microparticles were mixed with 3 ul of 1 mg/ml goat anti-rabbit IgG (3 ug), 10 ul of water, and 6 ul of WRK stocks to give 100 mM, 10 mM and 1 mM final concentration. After 30 min at 25° C., 950 ul of TBS was added and the samples spun in a microcentrifuge for 15 min. The pellets were resuspended in 60 ul TBS/0.1% Tween 20 and samples were tested in the lateral flow test (Example 7). By visual assessment the sample with 100 mM WRK clearly contained aggregates prior to centrifugation, and this was confirmed by the accumulation of material at the bottom of the lateral flow strip, as shown in FIG. 6.

EXAMPLE 12

Optimisation of Buffer for Reactions with Woodward's Reagent K 40 ul of succinylated 270 nm blue latex microparticles in water (prepared as described in Example 5) was mixed with 3 ul of 1 mg/ml goat anti-rabbit IgG (3 ug), 6 ul of 100 mM WRK (10 mM final concentration); and 10 ul of buffer selected from the following list: 1M MES pH 6.0; 1M MOPS pH 7.0; 1M MES pH 5.0. After conjugation for 30 min, washing with TBS, and centrifugation, each pellet was resuspended in 60 ul of TBS/0.1% Tween 20. Samples were tested in the lateral flow test (Example 7). Results are shown in FIG. 7. The greatest spot intensity was seen after reaction at pH 5.0.

EXAMPLE 13

Freeze Drying of Latex Microparticles with Woodward's Reagent K 200 ul of succinylated blue 270 nm dextran coated microparticles prepared as described in Example 4 were desalted into 400 ul of 25 mM MES, pH 5. 40 ul portions of desalted microparticles were mixed with 5 μl trehalose stock (1 g in 2 ml of water) and 5 ul of 100 mM WRK and frozen in liquid nitrogen. Freeze drying was performed according to the program in Example 6.

EXAMPLE 14

Freeze Drying of EDC with a Small Organic Dye

Carboxyfluorescein (Sigma C7153) was dissolved in 25 mM Epps pH 9.0 to give a 10 mM stock with a pH ~4.0. 0.5 ml of sample was diluted 0.5 ml of 100 mM EPPS pH 9.0 and 100 ul of trehalose stock (1 g plus 2 ml water) was added. The pH was measured as 7.71. EDC (11 ul of 1M stock) was added to 10 mM final concentration and 100 ul aliquots were freeze dried as described in Example 6. The freeze dried samples (2 tubes; both positive controls) were reacted with 100 ul of 500 kDa AM-Dextran in 50 mM MES pH 6.0 (prepared as described in Example 3) for 1 hour after which 100 ul 14.3 mM mercaptoethanol was added and the reaction was allowed to continue for a further 1 hour. In parallel with the above reactions, two tubes (both negative controls) of dried carboxyfluorescein/EDC mixture were each reconstituted with 100 ul of quencher (14.3 mM mercaptoethanol). After 1 hour, 100 ul of 500 kDa AM-Dextran in 50 mM MES pH 5.0 was added and the incubation was allowed to continue for a further hour. The contents of the positive and negative control tubes were pooled and exchanged into 500 ul TBS by desalting on separate NAP-5 columns. Fluorescence values (excitation 490 nm/emission 535) for 1/100 diluted positive and negative controls were 44129 and 229 (mean values, n=3), respectively.

EXAMPLE 15

Freeze Drying of EDC with a Protein Molecule

BSA (1 ml of 10% solution) was cationised by reaction for 4 hours at 25° C. with 9 ml of 0.5M MES/2 Methylene diamine, pH 6, plus 1 ml of EDC (1M). 1 ml of the reaction mix was desalted on a PD10 column into 1.25 ml of 10 mM EPPS, pH 8.5, to which was added 125 ul of trehalose stock (1 g in 2 ml water). Two 600 ul aliquots were dispensed into separate tubes; one tube (type A) was supplemented with 6 ul of 1M EDC and the other (type B) with 6 ul of water. Aliquots of 100 ul from each type were freeze dried according to the program in Example 6. Carboxyfluorescein was taken up in 100 mM MES pH 6 and 100 ul aliquots were added to one of each type of tube. After 30 min an equal volume of 10×TBS was added and the tubes were left overnight. Samples were desalted on NAP-5 columns into TBS. The fluorescence values measured as in Example 14 for 1/100 diluted samples of Type A and Type B were 33200 and 103 fluorescence units, respectively.

EXAMPLE 16

Coating of Gold Particles with BSA

Gold particles (200 ul of 15 OD material; either 20 nm or 40 nm naked gold; Bioassay Works) were added to 1 ml of 10 mg/ml BSA in water. After overnight incubation at 20° C. the samples were dialysed in tubing (Spectrum, product code 131486) against 2 changes of 1 L water (3 h per dialysis). The dialysed gold was brought to 10 mM EPPS by addition of 100 mM stock, pH 9. EDC was added to 1 mM from 10 mM stock. Finally trehalose was added to 3.33% w/v. Samples were frozen in liquid nitrogen and freeze dried according to the program in Example 6.

EXAMPLE 17

Production of Thiol/Amino Dextran

CM-Dextran (500 kDa) 1 ml was mixed with 200 ul of a mixed diamine solution prepared by combining, in a 20:80 volume ratio, solutions of 2M cystamine in 0.5M MES, pH 6.0 and 2 Methylene diamine in 0.5M MES, pH 6, and EDC from 1M stock to 100 mM final concentration. After incubation overnight at 25° C. the sample was desalted into 0.1M phosphate buffer pH 8.0 and DTT was added from 200 mM stock to a final concentration of 20 mM. After incubation for 1 hour at 25° C. the sample was desalted into 100 mM MES buffer pH 6 and used immediately for coating of gold particles as described in Example 18.

EXAMPLE 18

Coating of Gold Particles with Thiolated Dextran

Gold particles (15 OD) were diluted 1/10 with thiol/amino dextran prepared as described in Example 17 and incubated overnight at 25° C. For each ml of particles, 100 ul of 2M Hepes was added followed by succinic anhydride (from 1M stock in DMSO) to 100 mM final concentration. After 30 min, the material was washed by two cycles of centrifugation and washing with 20 mM MOPS buffer pH 7.2. To each ml of particles, 100 ul of trehalose stock (1 g in 2 ml of water) was added, followed by EDC (from 1M stock in water) to 10 mM concentration. The samples were freeze dried according to the program described in Example 6.

EXAMPLE 19 pH Control of Solutions Prepared from Buffer Concentrates

The following buffer concentrates were prepared 0.5M EPPS, 8.5; 1M MOPS pH 7.2; 1M Hepes, pH 7.5; 1M MES pH 6, and 0.5M CHES, pH 9.3. 1M EDC was prepared in water. Various buffer/EDC mixtures were prepared by appropriate dilution of stock substances to give either 0 mM, 1 mM or 10 mM EDC in 10 mM buffer. The pH values for the various solutions were (buffer; pH with 0 mM EDC; pH with 1 mM EDC; pH with 10 mM EDC): EPPS, 7.59, 7.67, 7.73; MOPS, 6.18, 6.25, 6.34; Hepes, 6.58, 6.64, 6.73; MES, 5.22, 5.29, 5.35; CHES, 8.64, 8.74, 8.82. One can see from these data that buffers other than EPPS with pKa values between pH 7 and 8 (e.g. MOPS, Hepes) could also be prepared as concentrates in the pH 8-8.5 range to achieve final pH values between pH 7 and pH 8.

EXAMPLE 20

Preparation of Concentrated Latex Microparticles 1 ml of 150 kDa AM-Dextran (Example 3) was mixed with 0.11 ml of trehalose (1 g in 2 ml water), frozen in liquid nitrogen, and freeze dried using the program given in Example 6. The dry powder was reconstituted with 1 ml of stock blue 270 nm carboxylated latex particles (Seradyn, product code 83100670020350) and incubated at room temperature for 24 hours before addition of 100 ul of 1M EDC. After incubation for 18 hours, 200 ul of 2M Hepes/10 mM EDTA was added, followed by 100 ul of succinic anhydride (1M) in DMSO. After 30 minutes at 25° C. the material was dialysed against three changes of 1 L of 25 mM MES buffer pH 6.0. 1 ml of dialysed sample was then buffer exchanged using a PD10 column into 1.5 ml 10 mM EPPS buffer. For each ml of microparticles in EPPS buffer, 100 ul of trehalose was added, followed by EDC from 1M stock to give a final concentration of 10 mM. Samples were freeze dried in aliquots of varying size using glass vials of an appropriate size. For example, 10 ul samples were dispensed into X-vials (Cronus, VZM-0309CF-100); 40 ul samples were dispensed into glass champagne vials (Cronus, VZM-1509CC-100); 0.4 ml volumes were freeze dried in 2 ml serum vials (Voigt 7010.90.0540), and 1 ml volumes were dispensed into 10 ml serum vials (Wheaton, 223686).

EXAMPLE 21

Conjugation with Freeze Dried ADP/EDC Mixtures 500 ul of 20 mM ADP monopotassium salt (Fluka product code 01899) was mixed with 200 ul of 0.5M EPPS pH 8.5, 100 ul of trehalose (1 g in 2 ml water), 200 ul of water and 5 µl of either 2M EDC (final concentration 10 mM) or water. Aliquots of 100 ul were freeze dried using the drying program given in Example 6. The two types of dry powders (i.e. with and without EDC) were reconstituted with 100 ul of cationised BSA prepared as described in Example 15 (but desalted into water instead of EPPS buffer) and 100 ul of 0.5M MES pH 6.2. After reaction for 18 hours at 25° C. free ADP was removed by desalting on a NAP-5 column (GE Healthcare) equilibrated with 0.15M NaCl. The fractions containing protein were pooled (0.3 ml) and subjected to acid hydrolysis by heating at 100° C. for 5 min with 75 ul of PiColorlock Gold colorimetric detection reagent for inorganic phosphate (Innova Biosciences product code 303-0030). Blank subtracted absorbance values ($A_{650}$) for 200 ul samples of hydrolysed BSA-ADP conjugates prepared either with or without EDC were 1.22 and 0.08, respectively.

The invention claimed is:

1. A method of producing a reagent for use in a conjugation reaction comprising
    a) forming a homogeneous solution or suspension of
        i) a carboxyl-activating or phosphate-activating non-enzymatic substance comprising 1-ethyl-3-(3-dimethylaminopropyl) carbodiimide hydrochloride (EDC), N-Cyclohexyl-N'-(β-[N-methylmorpholino]ethyl) carbodiimide (CMC), 1-ethyl-3-(4-azonia-4,4-dimethylpentyl)carbodiimide (EAC), 2,2-dichloro-5-(2-phenylethyl)-4-(trimethylsilyl)-3-furanone (DPTF), 4-(4,6-dimethoxy-1,3,5-triazin-2-yl)-4-methylmorpholinium chloride (DMT-MM), or N-ethyl-5-phenylisoxazolium-3'-sulphonate (Woodwards reagent K (WRK)), wherein the substance is capable of acting on a carboxyl group- or phosphate group-containing moiety to facilitate formation of (1) an amide bond between a carboxyl group and an amine group or (2) a phosphoramidate bond between a phosphate group and an amine group, and
        ii) a first reactant containing a carboxyl group or a phosphate group, or a second reactant containing an amine group; and
    b) drying the solution or suspension to produce the reagent comprising a homogeneous mixture of i) and ii).

2. The method according to claim 1, wherein the carboxyl-activating or phosphate-activating substance and the first or second reactant are mixed in the form of a solution.

3. The method according to claim 2, wherein the solution is an aqueous solution.

4. The method according to claim 1, wherein the drying comprises freeze drying.

5. The method according to claim 1, wherein the solution or suspension comprises a first reactant containing a carboxyl group or phosphate group.

6. The method according to claim 1, wherein first or second reactant in the solution or suspension comprises a coloured, fluorescent, enzyme, magnetic or particle label.

7. The method according to claim 1, wherein the first or second reactant in the solution or suspension comprises a microparticle.

8. The method according to claim 7, wherein the microparticle has a polymer coating.

9. The method according to claim 1, wherein the solution or suspension includes a polyhydroxylic material.

10. The method according to claim 1, wherein the solution or suspension includes a buffer.

11. The method according to claim 1, wherein the pH of the solution or suspension is greater than 4.

12. The method according to claim 11, wherein the pH is greater than 6.

13. The method according to claim 11, wherein the pH is greater than 7.

14. The method according to claim 11, wherein the pH is greater than 8.

15. A conjugation kit comprising the reagent produced by claim 1 and instructions for use.

16. A method of performing a conjugation reaction comprising using the conjugation kit of claim 15 in accordance with the instructions.

17. The method of claim 1 further comprising reconstituting the reagent in a liquid.

18. The method of claim 17 further comprising contacting the reconstituted reagent with a molecule to be conjugated.

19. The method of claim 1, wherein the solution or suspension excludes N-hydroxysuccinimide.

20. A method of producing a reagent for use in a conjugation reaction between a first reactant containing a carboxyl group or a phosphate group and a second reactant containing an amine group, comprising:
    a) forming a solution or suspension of
        i) a carboxyl-activating or phosphate-activating non-enzymatic substance capable of acting on a carboxyl group- or phosphate group-containing moiety to facilitate the formation of an amide bond between a carboxyl group and an amine group; or a phosphoramidate bond between a phosphate group and an amine group, and
        ii) the first reactant or the second reactant; and
    b) drying the solution or suspension to produce the reagent comprising a mixture of i) and ii),
    wherein said reagent excludes N-hydroxysuccinimide, and wherein the carboxyl-activating or phosphate-activating substance comprises 1 ethyl-3-(3-dimethylaminopropyl) carbodiimide hydrochloride (EDC), N-Cyclohexyl-N'-(β-[N-methylmorpholino]ethyl)carbodiimide (CMC), 1-ethyl-3-(4-azonia-4,4-dimethylpentyl)carbodiimide (EAC), 2,2-dichloro-5-(2-phenylethyl)-4-(trimethylsilyl)-3-furanone (DPTF), 4-(4,6-dimethoxy-1,3,5-triazin-2-yl)-4-methylmorpholinium chloride (DMT-MM), or N-ethyl-5-phenylisoxazolium-3'-sulphonate (Woodwards reagent K (WRK)).

* * * * *